(12) United States Patent
Freerksen et al.

(10) Patent No.: US 10,520,650 B2
(45) Date of Patent: Dec. 31, 2019

(54) EXTERNAL RESERVOIR CONFIGURATION FOR TUNABLE ACOUSTIC GRADIENT LENS

(71) Applicant: Mitutoyo Corporation, Kanagawa-ken (JP)

(72) Inventors: Isaiah Freerksen, Bothell, WA (US); Maxwell James Perkins, Mountlake Terrace, WA (US)

(73) Assignee: Mitutoyo Corporation, Kanagawa-ken (JP)

(*) Notice: Subject to any disclaimer, the term of this patent is extended or adjusted under 35 U.S.C. 154(b) by 52 days.

(21) Appl. No.: 16/000,319

(22) Filed: Jun. 5, 2018

(65) Prior Publication Data

US 2019/0369300 A1 Dec. 5, 2019

(51) Int. Cl.
| | |
|---|---|
| *G02B 3/00* | (2006.01) |
| *H04N 5/232* | (2006.01) |
| *G06T 7/00* | (2017.01) |
| *G02F 1/29* | (2006.01) |
| *G01N 21/88* | (2006.01) |
| *G02B 3/14* | (2006.01) |

(52) U.S. Cl.
CPC ....... *G02B 3/0087* (2013.01); *G01N 21/8806* (2013.01); *G02B 3/0081* (2013.01); *G02B 3/14* (2013.01); *G02F 1/29* (2013.01); *G06T 7/0004* (2013.01); *H04N 5/23212* (2013.01); *G02F 2001/294* (2013.01)

(58) Field of Classification Search
CPC .............. G02B 3/0087; G02B 27/0025; B29D 11/00355; H01L 27/14627; H01L 2924/0002

USPC .......................................................... 359/652
See application file for complete search history.

(56) References Cited

U.S. PATENT DOCUMENTS

| | | | |
|---|---|---|---|
| 7,627,162 | B2 | 12/2009 | Blanford et al. |
| 7,701,643 | B2 * | 4/2010 | Batchko ................... G02B 3/14 |
| | | | 359/665 |
| 8,194,307 | B2 | 6/2012 | Arnold et al. |
| 9,143,674 | B2 | 9/2015 | Gladnick |

(Continued)

OTHER PUBLICATIONS

Mermillod-Blondin et al., "High speed varifocal imaging with a tunable acoustic gradient index of refraction lens," *Optics Letters* 33(18):2146-2148, 2008.

*Primary Examiner* — Mohammed A Hasan
(74) *Attorney, Agent, or Firm* — Seed IP Law Group LLP

(57) ABSTRACT

A tunable acoustic gradient (TAG) lens is provided including a lens casing, a refractive fluid, a controllable acoustic wave generating element (e.g., a piezoelectric vibrator) and an external reservoir configuration. An operational volume of the refractive fluid is contained in a casing cavity of the lens casing. The external reservoir configuration includes a deformable external fluid reservoir that contains a reserve volume of the refractive fluid and that is connected to the casing cavity by a flow channel. The flow channel enables the refractive fluid to flow back and forth between the casing cavity and the deformable external fluid reservoir in accordance with expansion and contraction of the refractive fluid (e.g., due to changes in temperature). The lens casing, deformable external fluid reservoir and flow channel are configured as a sealed system, with no intentional gas volume included in the sealed system.

26 Claims, 8 Drawing Sheets

(56) References Cited

U.S. PATENT DOCUMENTS

| | | |
|---|---|---|
| 9,213,175 B2 | 12/2015 | Arnold |
| 9,256,009 B2 | 2/2016 | Theriault et al. |
| 9,736,355 B1 | 8/2017 | Bryll |
| 9,930,243 B2 | 3/2018 | Gladnick et al. |
| 2013/0141782 A1* | 6/2013 | Theriault ................. G02B 3/14 359/368 |
| 2013/0148196 A1* | 6/2013 | Arnold ................. G02B 21/025 359/385 |
| 2018/0180773 A1 | 6/2018 | Usami et al. |

\* cited by examiner

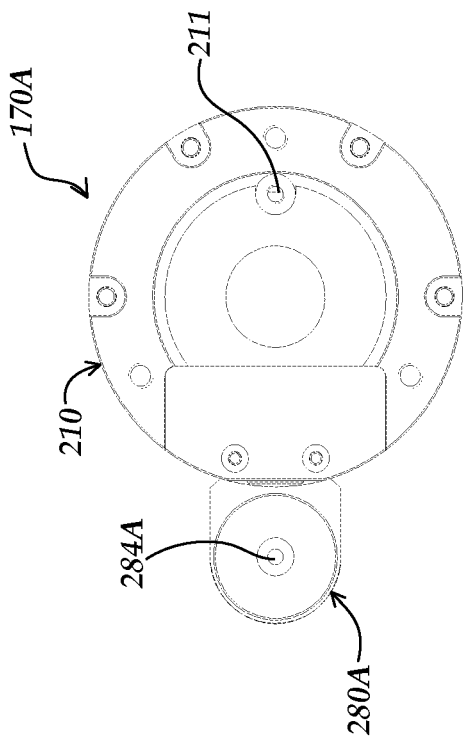
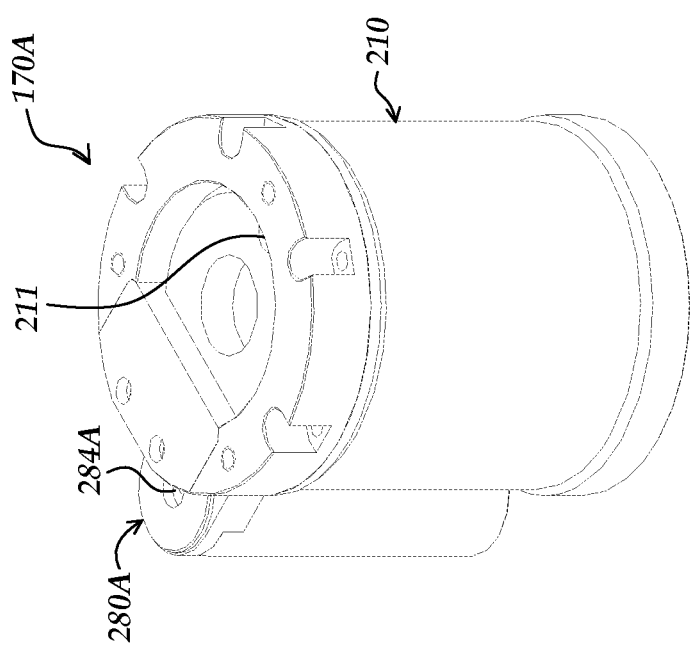
*Fig.3B.*
*Fig.3A.*

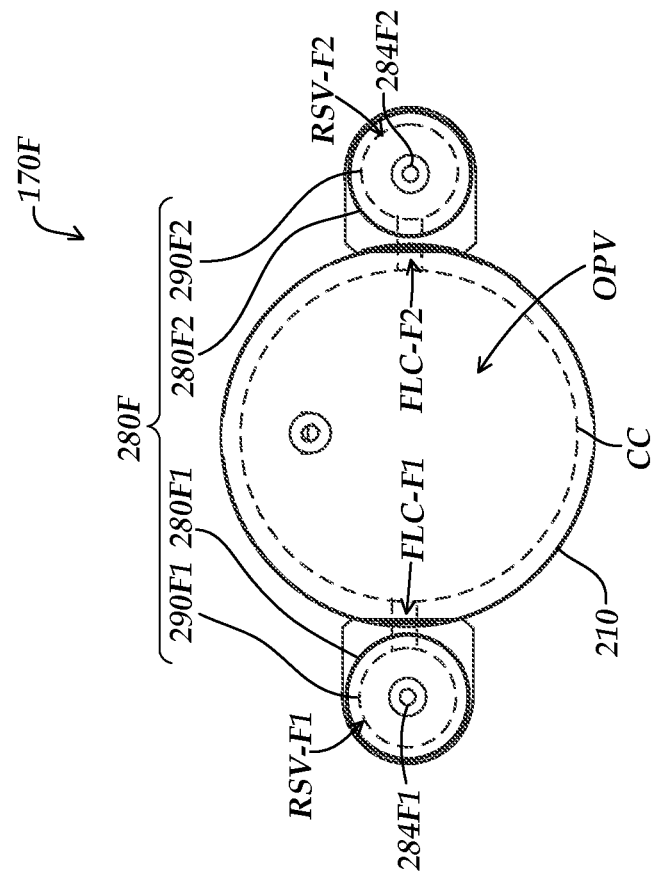
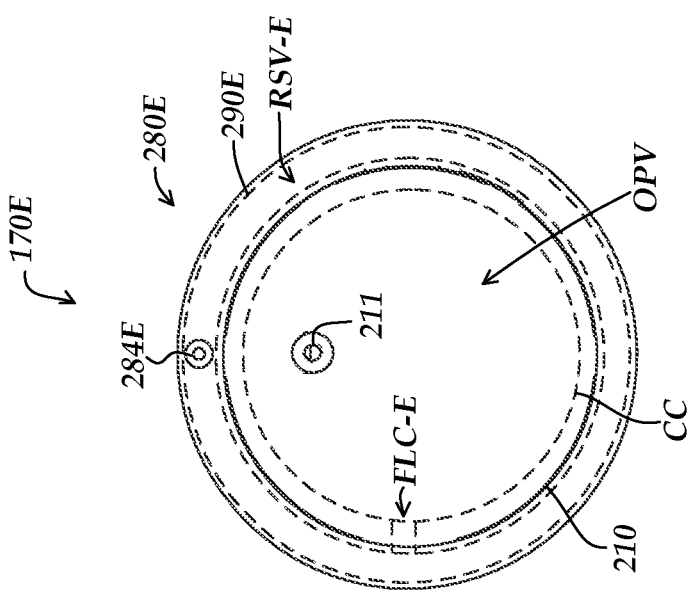
Fig. 8.
Fig. 7.

ent systems) where a TAG lens is precisely calibrated to correlate a particular optical power (or focus distance) with a particular phase of the resonant cycle, such a configuration exhibits undesirable instability and/or drift relative to that calibration. The calibration may be unstable during a turn on or warm up period, for example, or may drift over time or temperature.

EXTERNAL RESERVOIR CONFIGURATION FOR TUNABLE ACOUSTIC GRADIENT LENS

BACKGROUND

Technical Field

This disclosure relates to tunable acoustic gradient lenses, and more particularly to the use of tunable acoustic gradient lenses in variable focal length lens systems used for inspection and dimensional metrology.

Description of the Related Art

Various types of multi-lens variable focal length (VFL) optical systems may be utilized for observation and precision measurement of surface heights, and may be included in a microscope and/or precision machine vision inspection system, for example as disclosed in U.S. Pat. No. 9,143,674, which is hereby incorporated herein by reference in its entirety. Briefly, a VFL lens is capable of acquiring multiple images at multiple focal lengths, respectively. One type of known VFL lens is a tunable acoustic gradient ("TAG") lens that creates a lensing effect using sound waves in a fluid medium. The sound waves may be created by application of an electrical field at a TAG lens resonant frequency to a vibrating member (e.g., a piezoelectric tube) surrounding the fluid medium to create a time-varying density and index of refraction profile in the lens's fluid, which modulates its optical power and thereby the focal length or effective focus position of the vision system. A TAG lens may be used to periodically modulate a focus position at a resonant frequency of up to several hundred kHz, i.e., at a high speed. Such a lens may be understood in greater detail by the teachings in the article, "High speed varifocal imaging with a tunable acoustic gradient index of refraction lens" (Optics Letters, Vol. 33, No. 18, Sep. 15, 2008), and in U.S. Pat. Nos. 8,194,307, 9,213,175 and 9,256,009, each of which is hereby incorporated herein by reference in its entirety. Tunable acoustic gradient index lenses and related controllable signal generators are available, for example, from TAG Optics, Inc., of Princeton, N.J.

A TAG lens resonant frequency depends on several factors. For example, resonant frequency changes may result from changes in fluid medium properties and/or mechanical structure deformation due to pressure and/or temperature changes, for example. The aforementioned references teach including a compressible component such as bubble, or bladder or the like within the chamber of the TAG lens to compensate for changes that may occur within the closed lensing system. It is taught that the compressible component (e.g., a gas, a polymer, or a gel) may be a small controlled volume when compared to the volume of the fluid, and may therefore be located inside the sealed lens chamber of the TAG lens in a "partitioned reservoir" that prevents it from migrating to the optical performance path. It is also taught that the compressible component "alleviates the need to completely remove all air and/or other gases from the fluid prior to or after sealing the lens system." One exemplary prior system is described in U.S. Pat. No. 9,256,009, which is hereby incorporated herein by reference in its entirety.

The inventors have found that a TAG lens configured as outlined above provides sufficient resonance stability and optical performance for simple imaging applications (e.g., where the primary purpose is observation), and/or when operating within a limited temperature range. However, it has been found that in metrology systems (e.g., microscope systems) where a TAG lens is precisely calibrated to correlate a particular optical power (or focus distance) with a particular phase of the resonant cycle, such a configuration exhibits undesirable instability and/or drift relative to that calibration. The calibration may be unstable during a turn on or warm up period, for example, or may drift over time or temperature.

A configuration that can provide improvements with regard to such issues for TAG lenses would be desirable.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A tunable acoustic gradient (TAG) lens is provided including a lens casing, a refractive fluid, a controllable acoustic wave generating element and an external reservoir configuration. The lens casing has a casing cavity, and an operational volume of the refractive fluid is contained in the casing cavity. The controllable acoustic wave generating element (e.g., a piezoelectric vibrator) is arranged inside the lens casing around an optical path that passes through the operational volume. The external reservoir configuration includes a deformable external fluid reservoir that is connected to the casing cavity by a flow channel through the lens casing. In various implementations, the external reservoir configuration may be provided as a separate element (e.g., as an accessory, or upgrade element, etc.) that is connectable to the lens casing of a TAG lens.

The deformable external fluid reservoir of the external reservoir configuration contains a reserve volume of the refractive fluid, and the flow channel enables the reserve volume of refractive fluid to flow back and forth between the casing cavity and the deformable external fluid reservoir in accordance with expansion and contraction of the refractive fluid in the lens casing, as occurs due to changes in the operating or environmental temperature of the TAG lens. The lens casing, the deformable external fluid reservoir and the flow channel are configured as a sealed system. The operational volume of the refractive fluid is capable of changing its refractive index along the optical path in response to application of an acoustic wave by the acoustic wave generating element, in accordance with which the TAG lens is controlled to provide a periodically modulated optical power variation for the TAG lens.

In contrast to known TAG lens systems and teachings, according to principles disclosed herein, no gas volume or other compressible component is located inside the refractive fluid of the TAG lens, therefore no partitioned reservoir is required to prevent it migrating to the "optical performance path" of the TAG lens. Contrary to known TAG lens systems and teachings, in configurations disclosed herein it is possible to completely remove all air and/or other gases from the fluid prior to sealing the lens system. In various implementations, this may be desirable for reducing the appearance and migration of small bubbles in the "optical performance path" of the TAG lens over time due to outgassing and/or cavitation, or the like. Contrary to known TAG lens systems and teachings wherein the compressible component is limited to a small controlled volume when compared to the volume of the fluid, in configurations disclosed herein the external fluid reservoir accommodates large fluid volume changes in comparison to the operational fluid volume of the TAG lens. Furthermore, such large fluid volume changes may be achieved without a significant change in fluid pressure in the operational fluid volume of the TAG lens. In some implementations, the fluid pressure may be maintained at approximately atmospheric pressure, or at a desired approximately constant pressure that is different than atmospheric pressure. In various implementations, the external fluid reservoir may be provided as an optional accessory or component of a TAG lens, and may be retrofitted to "simple imaging" TAG lenses that are desired to be converted to more precise and stable operation.

BRIEF DESCRIPTION OF THE SEVERAL VIEWS OF THE DRAWINGS

FIGS. 3A and 3B are diagrams of isometric and top views of a TAG lens with a generic implementation of an external reservoir configuration;

FIG. 7 is a diagram of a top view of a TAG lens with a fourth exemplary implementation of an external reservoir configuration;

FIG. 8 is a diagram of a top view of a TAG lens with a fifth exemplary implementation of an external reservoir configuration.

DETAILED DESCRIPTION

Figure 1:
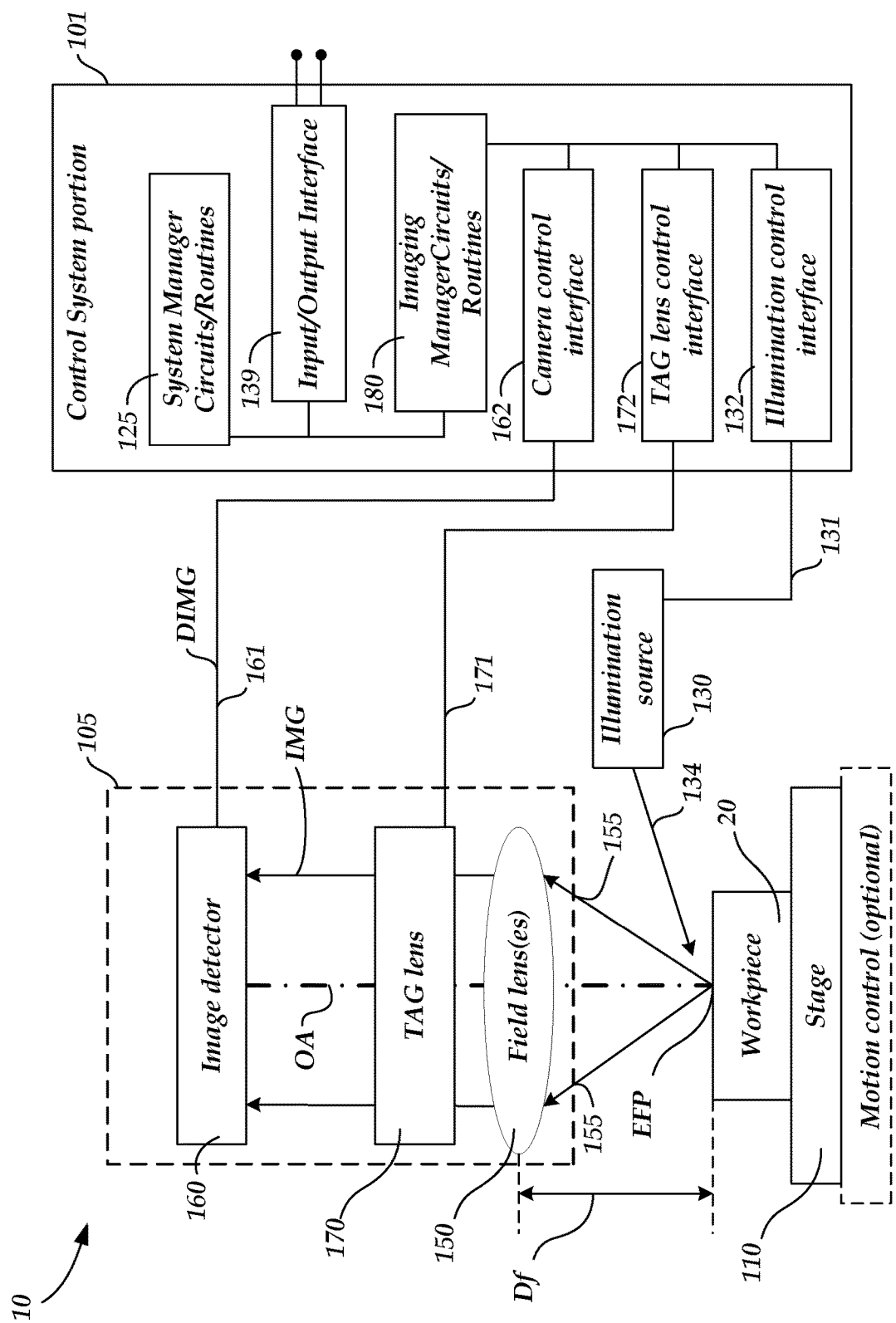
FIG. 1 is a block diagram of an optical imaging system portion and a control system portion of an imaging/inspection system.
Figure 2:
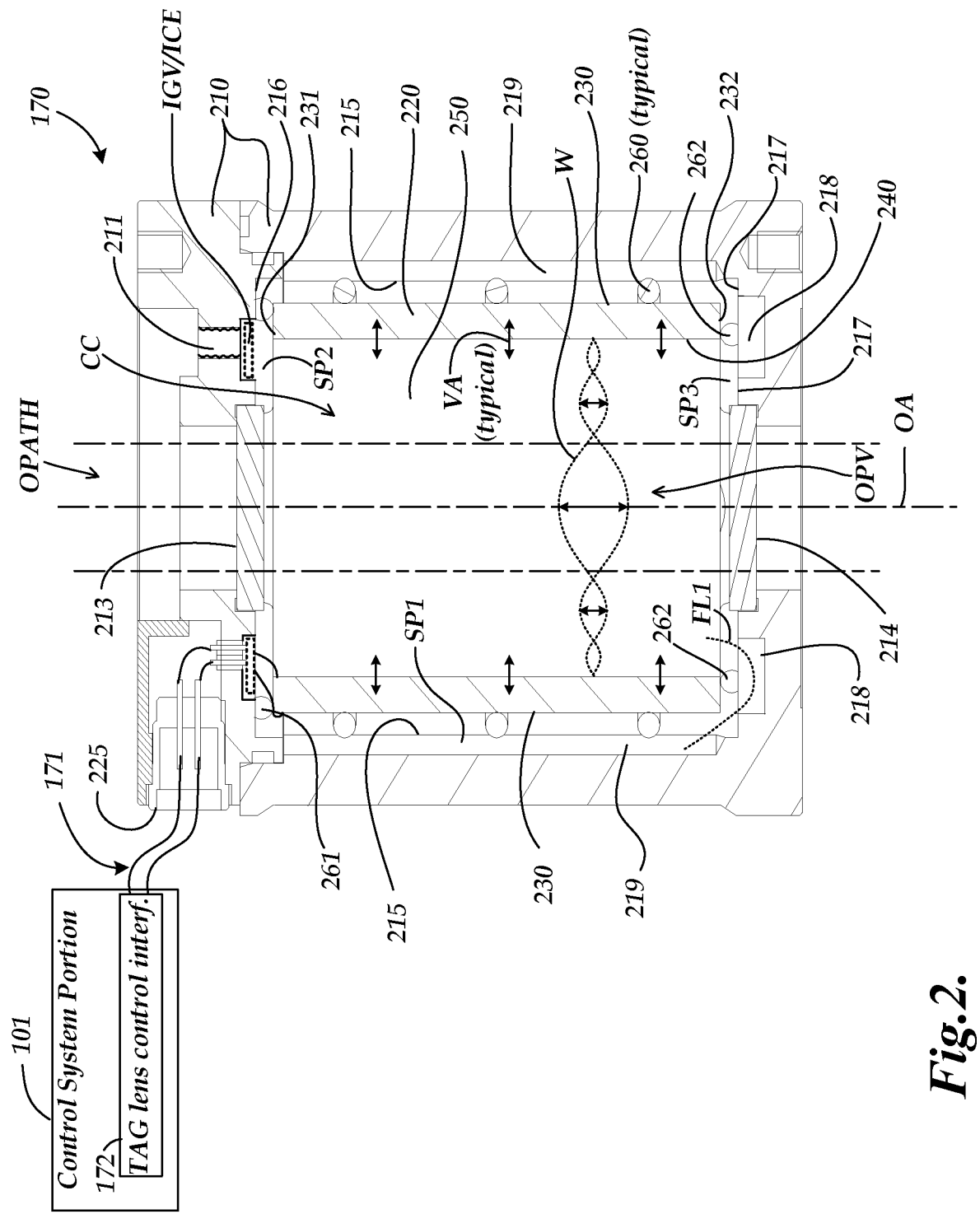
FIG. 2 is a diagram of a cross section of a TAG lens including known features, including a representation of a known compressible element and a standing acoustic wave generated at resonance therein.

The description of FIGS. 1-3 provides a brief background regarding various operating principles and applications of a TAG lens used in a workpiece inspection system. To supplement this brief background with more in-depth explanation and understanding, various aspects of such operating principles and applications are described in greater detail in the previously incorporated references, and in U.S. Pat. Nos. 9,930,243; 9,736,355; 7,627,162, each of which is hereby incorporated herein by reference in its entirety.

FIG. 1 is a block diagram of an imaging/inspection system 10 including an optical imaging system 105, an illumination source 130, a workpiece stage 110 and a control system portion 101. In various implementations, the imaging/inspection system 10 may be adapted to a machine vision host system, or used as a standalone system, and may be operated according to principles disclosed herein and in the incorporated references. The imaging/inspection system 10, including the optical imaging system 105, the illumination source 130, and the workpiece stage 110, may generally be controlled by the control system portion 101 to image or inspect a workpiece 20.

The optical imaging system 105 includes an image detector 160 (e.g., a camera), one or more field lenses 150 (e.g., including an interchangeable objective lens), and a TAG lens 170. The control system portion 101 may include system manager circuits/routines 125, which may govern an input/output interface 139, and imaging manager circuits/routines 180. A host system, or various individual display devices or input devices, or the like, may be connected to the input/output interface 139. In some implementations the workpiece stage 110 may comprise an (optional) motion control system that moves the workpiece relative to the optical imaging system 105. In such implementations, the system manager circuits and routines 125 may include a workpiece program generator and executor (not shown), that operates the motion control system and other features of the imaging/inspection system 10, to automatically inspect the workpiece 20, as disclosed in the incorporated references. As shown in FIG. 1, the imaging manager circuits/routines 180 includes or governs an illumination control interface 132, a camera control interface 162, and a TAG lens control interface 172. The TAG lens control interface 172 may include or be connected to a TAG lens controller (e.g., in a portion of the imaging manager circuits/routines 180) including circuits and/or routines for controlling various image exposures synchronized with the periodic focus position modulation provided by the TAG lens 170. In some implementations, the TAG lens control interface 172 and a TAG lens controller may be merged and/or indistinguishable. The illumination control interface 132 may control, for example, the selection, power, on/off switch, and strobe pulse timing, if applicable, for corresponding illumination sources (e.g., illumination source 130). In some implementations, the illumination control interface 132 may include an exposure (strobe) time controller or may otherwise provide strobe timing signals (e.g., to the illumination source 130), such that they provide an image exposure strobe timing that is synchronized with a desired phase timing of the TAG lens focus position modulation. The camera control interface 122 may control, for example, the camera configuration, exposure timing, and data output and the like, if applicable. In some implementations, the camera control interface 162 may include a timing controller such that the camera image exposure timing is synchronized with a desired phase timing of the TAG lens focus position modulation and/or an illumination timing.

Each of these components, as well as the additional components described below, may be interconnected by one or more data/control busses and/or application programming interfaces, or by direct connections between the various elements.

As will be described in more detail below, an imaging optical path OPATH (along the optical path OA) comprises various optical components that convey workpiece imaging light 155 from the workpiece 20 to the image detector 160. For example, the field lens 150, TAG lens 170 and image detector 160 may all be arranged with their optical axes aligned on the same optical axis OA that intersects with the surface of the workpiece 20. However, it will be appreciated that this implementation is intended to be exemplary only, and not limiting. More generally, the imaging optical path OPATH may include mirrors and/or other optical elements, and may take any form that is operational for imaging the workpiece 20 using an image detector (e.g., the image detector 160) according to known principles. In the illustrated implementation, the imaging optical path OPATH includes the TAG lens 170, and may be utilized for imaging and/or measuring a surface of a workpiece 20 using one or more workpiece image exposures.

As previously outlined, the optical power of the TAG lens 170 changes continuously at a high frequency in response to a resonant drive signal (e.g., as input on a signal line 171 from a TAG lens control interface 172 of the control system portion 101). The effective focus position EFP changes accordingly. In various implementations, the drive signal is a sinusoidal AC signal at a resonant frequency of operation of the TAG lens 170. A focal length Df corresponding to an effective focus position EFP is available at a correspond time or "phase timing" during the sinusoidally changing the optical power of the TAG lens 170. The nominal or "mid-range" effective focus position may be considered to be the (fixed) focal length of the field lens 150 (e.g., an objective lens), in combination with the TAG lens in a state where its optical power is zero. The illumination source 130 or the image detector 160 may be "strobed" at a particular phase or "phase timing" of the resonant cycle to obtain an image exposure focused at a corresponding effective focus position or focus distance. The source light 134 is reflected or transmitted as workpiece light 155, and the workpiece light used for imaging passes through the field lens 150 and the TAG lens 170 and is gathered by the image detector 160 (e.g., a camera). A workpiece image exposure which includes the image of the workpiece 20 is captured by the image detector 160, and is output on a signal line 161 to the imaging manager circuit/routines 180 (e.g., through a camera control interface 162). In various implementations, the image detector 160 may be a known charge coupled device (CCD) image sensor or other form of camera, and may receive an incident image IMG and may output to the imaging manager circuit/routines 180 a detected image DIMG having a predetermined signal form.

Known contrast-based focus analysis methods may be used to analyze the resulting image(s) and determine whether they are in focus, and/or may be used in the system manager circuits and routines 125 or the imaging manager circuits/routines 189 to adjust the strobe phase timing to provide an "autofocus" operation that provides a focused image of the workpiece 20. Alternatively, or in addition, such contrast-based focus analysis methods may be used to identify a best-focus image out of a set of images acquired at a corresponding set of known phase timings, and output that "best-focus" phase timing value. Z-height (effective focus position) calibration data may be utilized that relates respective Z-heights or effective focus positions to respective "best-focus" phase timings. Thus, the surface height coordinate of an imaged surface portion of a workpiece 20 may be determined based on the phase timing associated with its "best focus" image. Therefore, the optical imaging system 105 and/or the imaging/inspection system 10 may be used to measure or profile the workpiece 20 by scanning across it, if desired. Various aspects of such measuring processes are described in greater detail in the incorporated references.

Based on the foregoing description of height measurement, it will be understood that if the TAG lens operating characteristics drift, its actual operating characteristics may deviate from its calibration data, resulting in inaccurate height measurements. As previously indicated, the inventors have found that in metrology systems (e.g., microscope systems) where a TAG lens is precisely calibrated to correlate a particular optical power and/or focus distance with a particular phase of the resonant cycle, previously known TAG lens configurations do indeed exhibit undesirable instability and/or drift relative to that calibration. A known TAG lens configuration is described with reference to FIG. 2. Configurations according to principles disclosed herein, which provide more stable operating characteristics over a range of operating conditions, are described with reference to FIGS. 3 through 9.

FIG. 2 is a diagram of a cross section of a TAG lens 170 including known features, including a representation of a known intentional gas volume or intentional compressible element IGV/ICE (hereafter referred to simply as compressible element IGV/ICE) and a standing acoustic wave W generated at resonance therein. The TAG lens 170 includes a lens casing 210, a controllable acoustic wave generating element 220, and a refractive fluid 250.

As illustrated in FIG. 2, the casing cavity CC of the lens casing 210 includes an operational volume OPV of the refractive fluid 250, and the acoustic wave generating element 220 (e.g., a piezoelectric vibrator) is arranged inside the lens casing 210 around an optical path OPATH that passes through the operational volume OPV. In various implementations, the lens casing 210 may be a hollow cylindrical case, and the controllable acoustic wave generating element 220 may be a hollow cylindrical piezoelectric vibrator that is installed on the interior of the lens casing 210. In various alternative implementations, the lens casing 210 may have other shapes (e.g., a hollow hexagonal shape, etc.). In various implementations, the controllable acoustic wave generating element 220 may be supported by spacers 260, 261 and 262 (e.g., O-rings used only for mechanical support, made of an elastomer, etc.). In various implementations, one or more spacers 260 may be disposed between an outer circumferential surface 230 of the controllable acoustic wave generating element 220 and an inner circumferential cavity wall 215 of the lens casing 210 (e.g., forming a spacing SP1). Similarly, one or more spacers 261 may be disposed between an upper surface 231 of the controllable acoustic wave generating element 220 and an upper inner surface 216 of the lens casing 210 (e.g., forming a spacing SP2), and one or more spacers 262 may be disposed between a lower surface 232 of the controllable acoustic wave generating element 220 and a lower inner surface 217 of the lens casing 210 (e.g., forming a spacing SP3).

In various implementations, the controllable acoustic wave generating element 220 vibrates in a thickness direction due to a drive signal (e.g., an AC voltage that is applied between the outer circumferential surface 230 and the inner circumferential surface 240). In various implementations, the drive signal is applied through a signal line (e.g., signal line 171 of FIG. 1, as provided from the TAG lens control interface 172 of the control system portion 101) and through the electrical connector 225 to the acoustic wave generating element.

In various implementations, the drive signal (e.g., comprising an AC voltage) that is provided on the signal line 171 may be adjusted to a resonant frequency that produces a standing acoustic wave W in the refractive fluid 250 on the inner side of the controllable acoustic wave generating element 220 (i.e., within the portion of the casing cavity that is surrounded by the inner circumferential surface 240). In such a case, when the controllable acoustic wave generating element 220 is vibrated as indicated by representative vibration arrows VA, a standing acoustic wave W arises in the refractive fluid 250 (i.e., and concentric circular wave regions arise where the refractive index increase and decreases). It will be understood that the standing acoustic wave W produces a density gradient that provides a refractive index distribution corresponding approximately to the standing acoustic wave W. The central portion of that refractive index distribution, represented as the optical path OPATH between the vertical dashed lines, may be used for imaging.

As noted above, the casing cavity CC (e.g., as formed by the inner circumferential cavity wall 215 and the upper and lower surfaces 216 and 217) is filled with the refractive fluid 250. In various implementations, the refractive fluid 250 may be added to the casing cavity CC through one or more inlet/outlet ports (e.g., including an inlet/outlet port 211), which are then sealed. In various implementations, under desired operating conditions, the entire controllable acoustic wave generating element 220 is immersed in the refractive fluid 250, such that the cavity within the hollow cylindrical controllable acoustic wave generating element 220 (i.e., as surrounded by the inner circumferential surface 240) is filled with the refractive fluid 250. The horizontal and vertical slots or channels 218 and 219 in the lens casing 210 allow the refractive fluid 250 to flow to surround the outer circumferential surface 230 of the acoustic wave generating element 220 at the time of filling. In contrast to the spacing SP1, which extends around the entire outer circumference of the acoustic wave generating element 220, it will be appreciated that the vertical channel(s) 219 are discrete channels (e.g., vertical slots formed by drilling or other processes in the lens casing 210). The refractive fluid 250 is able to flow from the cavity within the inner circumferential surface 240 into the vertical channel(s) 218 and through the spacings SP (e.g., spacings SP1 and SP3) produced by the spacers (e.g., spacers 260 and 262) and into the vertical channel(s) 219. In this manner, the refractive fluid 250 is also able to fill the spacings SP1, SP2 and SP3 between the acoustic wave generating element 220 and the inner circumferential cavity wall 215 and the upper and lower inner surfaces 216 and 217 of the casing cavity CC of the lens casing 210, so as to surround the outside of the acoustic wave generating element 220. The TAG lens 170A also includes upper and lower windows 213 and 214, that are disposed at upper and lower portions of the casing cavity CC, respectively, and sealed against it. The optical path OPATH that passes through a center of the TAG lens 170A (e.g., as centered along the optical axis OA) passes through the upper and lower windows 213 and 214.

It should be appreciated that the resonant frequency outlined previously is a property of the overall system, and is sensitive to variations in factors such as temperature, and/or pressure, and/or mechanical stresses. The lensing characteristics of the resulting standing acoustic wave W are similarly sensitive. Therefore, as previously indicated, the TAG lens 170 may vary from the operating state used to establish the aforementioned calibration data (the data that characterizes the effective focus position EFP or optical power vs. phase timing values), and height measurement errors may arise as a result. The resulting errors may be small, but they are significant in precision measurement applications. The various principles and configurations disclosed herein are directed to reducing variations in the driving factors noted above, as well as to reducing variations due to movement and/or inadequacy of the previously known compressible element IGV/ICE, or the like (described further below.) Regarding the previously known compressible element IGV/ICE, the state of the art is represented in FIG. 2 by dashed outlines which represent an approximate cross section of an annular shape and intentional gas volume, or a closed-cell compressible element, or the like. Ideally the compressible element IGV/ICE is isolated in a corresponding annular groove as shown—at least under ideal operating conditions (e.g., where the TAG lens is used in an upright orientation, as illustrated.) When the compressible element is an intentional gas volume, one procedure that has been used is to fill the casing cavity CC 100% with refractive fluid 250, and then extract a desired volume, prior to sealing. This leaves the intentional gas volume in the sealed casing cavity CC, where it will fill the corresponding annular groove, as illustrated. Some features of various implementations of the compressible element IGV/ICE have now been shown to be undesirable. One undesirable feature is that an intentional gas volume may move (e.g., when the TAG lens 170 is tilted), or dissolve into the refractive fluid 250 and subsequently be released into the optical path OPATH by cavitation. Another undesirable feature is that the compressible element IGV/ICE is only compressible as a result of a pressure increase—which is already an undesirable variation. Another undesirable feature is that the size of the compressible element IGV/ICE is limited, and thus restricts the allowed operating conditions of the TAG lens 170. Thus, the known compressible element IGV/ICE only mitigates actual variations and problems; it does not prevent their occurrence. The various features and principles disclosed below are intended to overcome and/or prevent such problems.

FIGS. 3A and 3B are diagrams of isometric and top views of a TAG lens 170A with a lens casing 210 and a generic implementation of an external reservoir configuration 280A. It will be appreciated that certain numbered components 2XX or 2XXA of FIGS. 3A and 3B may correspond to and/or have similar operations as identically or similarly numbered counterpart components 2XX of FIG. 2, and may be understood by analogy thereto and as otherwise described below. This numbering scheme to indicate elements having analogous design and/or function is also applied to the following FIGS. 4-8 (e.g., for components 2XXB, 2XXC, 2XXD, 2XXE, 2XXF, etc.).

As illustrated in FIGS. 3A and 3B, in various implementations, an external reservoir configuration 280A (as including a deformable external fluid reservoir, described further below) may be located to one side of the outside of the lens casing 210. Additional examples of such implementations will also be described in more detail below with respect to FIGS. 4-8. As will be described in more detail below with respect to FIGS. 7 and 8, in various alternative implementations, different configurations may be implemented (e.g., an external fluid reservoir may extend around at least a portion of a lens casing, and/or multiple external fluid reservoirs may be disposed around a lens casing, etc.).

As shown in FIGS. 3A and 3B, the lens casing 210 includes at least one inlet/outlet port 211, and the external reservoir configuration 280A includes at least one inlet/outlet port 284A. In various implementations, the inlet/outlet ports 211 and 284A are utilized in combination for initially adding refractive fluid 250 to the casing cavity of the lens casing 210 and/or the deformable external fluid reservoir inside the external reservoir configuration 280A, as will be described in more detail below with respect to FIG. 4. The inlet/outlet ports 211 and 284B are closed/sealed after the refractive fluid 250 has filled the casing cavity and/or the deformable external fluid reservoir. In various implementations, the external reservoir configuration 280A may be fixedly attached to the lens casing 210 utilizing various configurations (e.g., bolts, welding, etc.).

Figure 4:
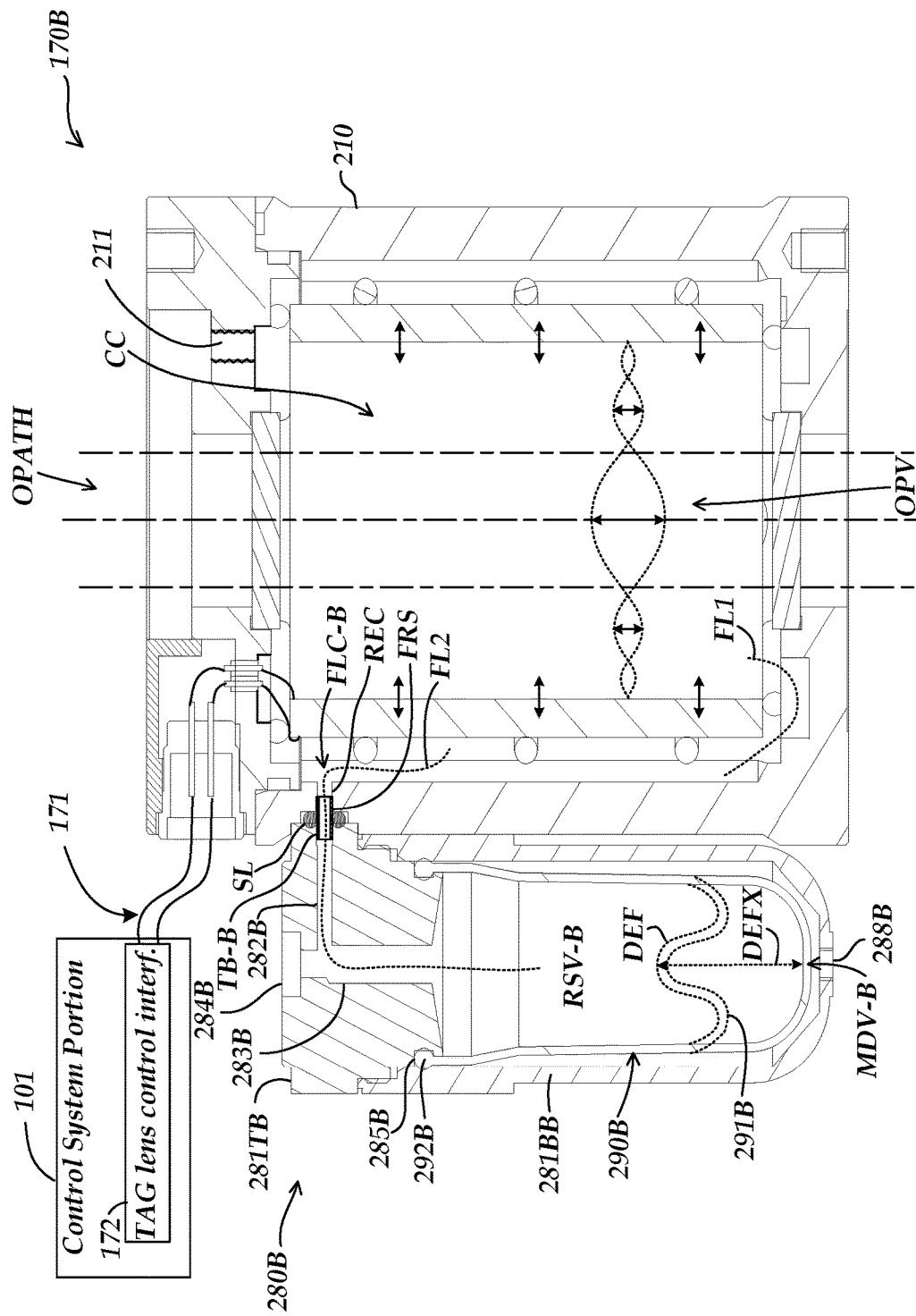
FIG. 4 is a diagram of a cross section of a TAG lens with a first exemplary implementation of an external reservoir configuration.
Figure 5:
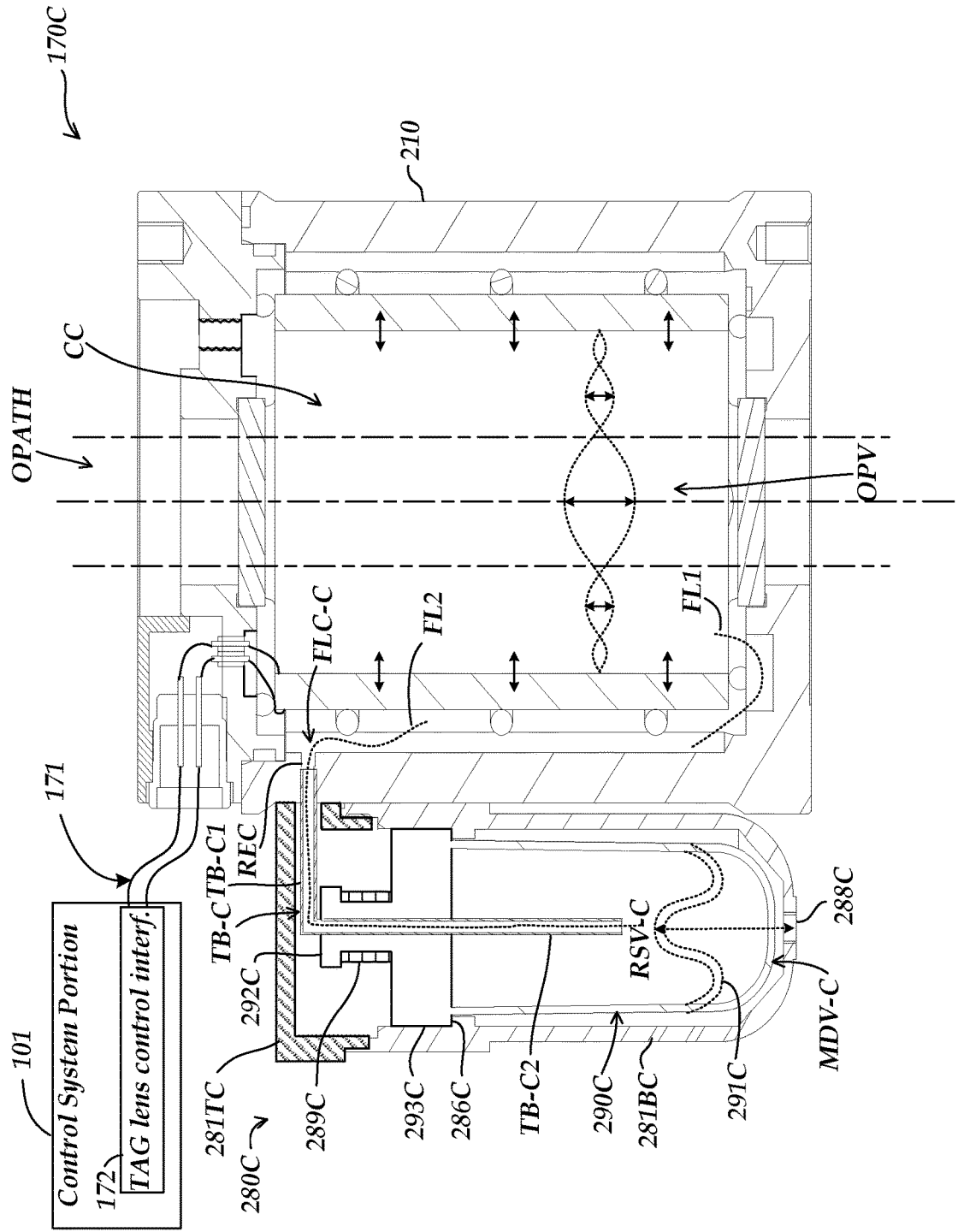
FIG. 5 is a diagram of a cross section of a TAG lens with a second exemplary implementation of an external reservoir configuration.
Figure 6:
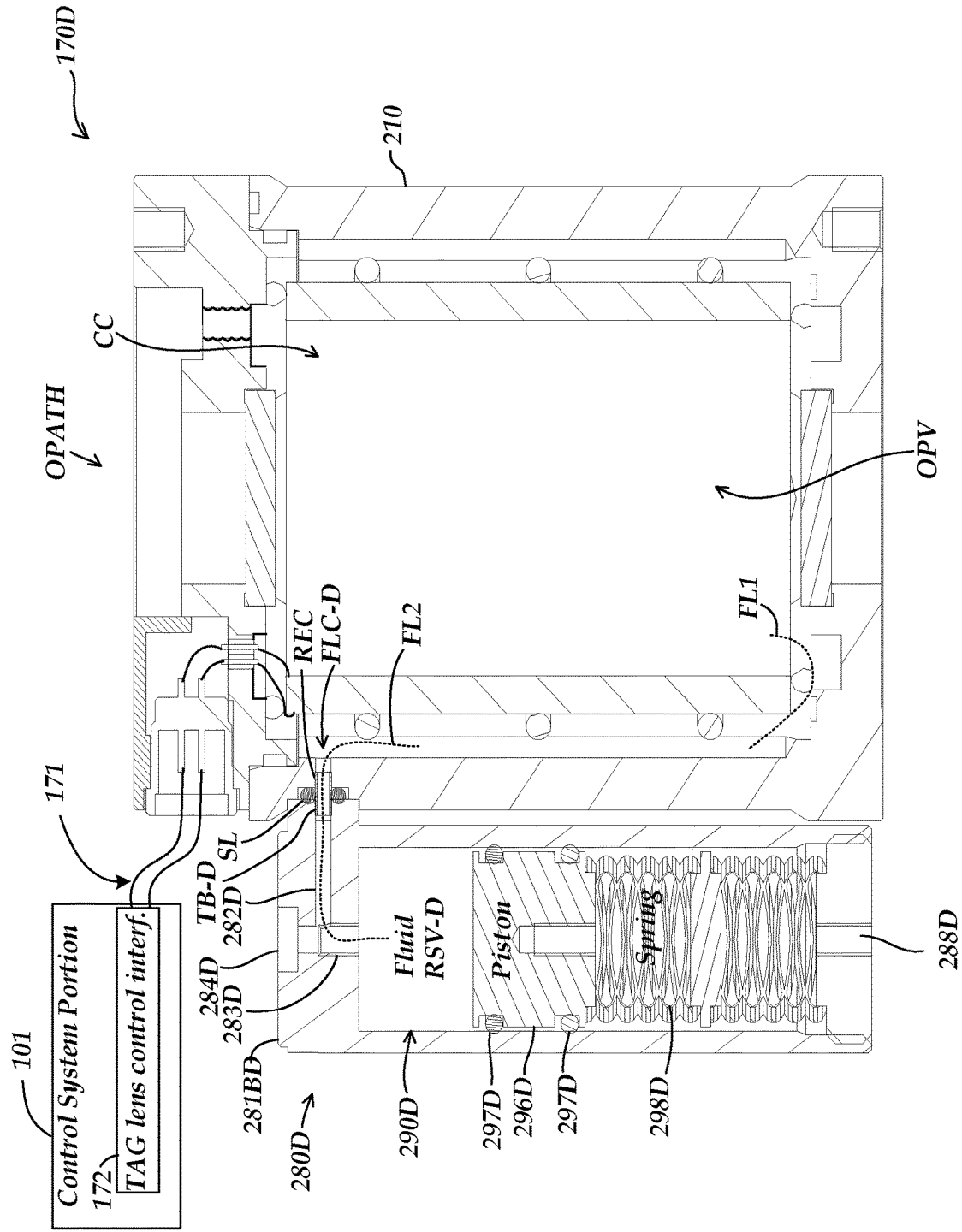
FIG. 6 is a diagram of a cross section of a TAG lens with a third exemplary implementation of an external reservoir configuration.

FIG. 4 is a diagram of a cross section of a TAG lens 170B with a first exemplary implementation of an external reservoir configuration 280B. In FIGS. 4-6, the components and configurations within the lens casing 210 will be understood to be similar or identical to those of FIG. 2, except as otherwise described below. As illustrated in FIG. 4, the external reservoir configuration 280B comprises an external reservoir body 281BB, which is sealed against an external reservoir top 281TB (e.g., a manifold), and a deformable external fluid reservoir 290B. The deformable external fluid reservoir 290B (e.g., and elastomeric bladder) contains a variable reserve volume RSV-B that expands when the deformable external fluid reservoir 290B receives refractive fluid 250 from the casing cavity CC, and that contracts when refractive fluid 250 flows from the deformable external fluid reservoir 290B to the casing cavity CC. Such fluid exchange may be driven by thermal expansion/contraction of the refractive fluid in the "rigid" casing cavity CC, for example.

In the illustration of FIG. 4, example deformation lines DEF schematically illustrate a deformation (a contraction) of a deformable portion 291B of the deformable external fluid reservoir 290B, which may occur at a particular overall fluid volume of the TAG lens 170B (e.g., as influenced by operating temperature.) A deformation arrow DEFX schematically illustrates how the deformable portion 291B may contract and/or expand to a maximum design volume MDV-B of the deformable external fluid reservoir 290B (e.g., corresponding to the entire available reserve volume within the external reservoir configuration 280B). In various implementations, the deformable portion 291B may include a lip portion 292B that is received in and sealed against an indented portion 285B of the external reservoir top 281TB. In the implementation of FIG. 4, the flow channel FLC-B comprises a tube TB-B that extends between the lens casing 210 (e.g., extending into the reservoir exchange channel REC) and the external reservoir configuration 280B, and through which the refractive fluid is enabled to flow back and forth between the casing cavity CC and the external reservoir configuration 280B. One or more sealing elements SL (e.g., sealing rings) may be included (e.g., as located around the tube TB-B and for sealing the connection between the lens casing 210 and the external reservoir configuration 280B) to ensure sealed containment of the refractive fluid 250. The external reservoir top 281TB (e.g., a manifold) includes a horizontal channel 282B and a vertical channel 283B, through which the refractive fluid 250 is able to flow back and forth between the tube TB-B and the deformable external fluid reservoir 290B. A flow line FL2 illustrates a flow of the refractive fluid 250 between the casing cavity CC and the deformable external fluid reservoir 290B, as passing through the flow channel FLC-B.

In various implementations, the flow channel FLC-B has at least one flow restricting section FRS (e.g., as part of the reservoir exchange channel REC or other portion of the flow channel FLC-B) that is configured to be small enough to minimize system damping effects and/or energy loss during resonance of the refractive fluid 250 in the lens casing 210 when an acoustic wave is applied by the acoustic wave generating element 220, as may be determined by analysis and/or experiment. It will be appreciated that such implementations are also configured to enable the flow of expanding or contracting refractive fluid to keep up with the expected rate of temperature changes that may occur during the operation or transport of the TAG lens 170B. In various implementations, the flow restricting section FRS may have a cross-sectional flow area of at most 25 square millimeters, or alternatively at most 15 square millimeters (e.g., so as to achieve the above noted design parameters including isolating resonance of the refractive fluid 250 in the lens casing 210 while also allowing enough flow to minimize pressure changes of the refractive fluid 250 in the lens casing 210 that may otherwise occur due to temperature changes, etc.).

In various implementations, the deformable external fluid reservoir 290B is configured to maintain an approximately constant pressure of the refractive fluid 250 in the casing cavity CC over at least a range of temperatures between −20 degrees C. and 60 degrees C. In various implementations, the external reservoir configuration 280B is configured with atmospheric pressure acting on the outside of the deformable portion 291B at all operating temperatures. For example, a vent 288B may be provided in a portion (e.g., a lower portion) of the external reservoir body 281BB, which opens to the atmosphere and which is configured to allow atmospheric pressure to act on the outside of the deformable external fluid reservoir 290B. In various implementations, the vent 288B is configured to maintain the refractive fluid in the casing cavity CC at a pressure of approximately 1 atmosphere regardless of an operating temperature of the TAG lens.

In various implementations, the lens casing 210 includes at least one inlet/outlet port 211 and the external reservoir configuration 280B includes at least one inlet/outlet port 284B. In various implementations, the inlet/outlet ports 211 and 284B are utilized in combination for initially adding refractive fluid 250 to at least one of the casing cavity CC or the deformable external fluid reservoir 290B, wherein the inlet/outlet ports 211 and 284B are closed/sealed after the refractive fluid 250 has filled the casing cavity CC and/or the deformable external fluid reservoir 290B. For example, the inlet/outlet ports 211 and 284B may initially be opened as part of a process for adding refractive fluid 250 to the TAG lens 170B. After an initial combined fluid volume is established (e.g., including the operational volume OPV and the reserve volume RSV), the total amount of fluid is kept constant and the inlet/outlet ports 211 and 284B that are used for initially filling the TAG lens 170B remain sealed. It will be appreciated that in contrast to the inlet/outlet ports 211 and 284B, in various implementations the reservoir exchange channel REC (i.e., that extends through the lens casing 210 and is part of the flow channel FLC) is not an externally accessible port and is not usable as an inlet/outlet port for adding or removing refractive fluid 250 from the TAG lens 170B.

In various implementations, the variable ratio of the operational volume OPV to the reserve volume RSV varies depending at least in part on the temperature of the refractive fluid 250. In various implementations, the deformable external fluid reservoir 290B is configured to maintain an approximately constant pressure of the refractive fluid 250 in the casing cavity CC. For example, when the temperature of the refractive fluid 250 in the casing cavity CC increases and causes the refractive fluid 250 to expand, at least some of the refractive fluid 250 flows from the casing cavity CC to the deformable external fluid reservoir 290B (e.g., so as to maintain the pressure of the refractive fluid 250 in the casing cavity CC at an approximately constant level). Similarly, when the temperature of the refractive fluid 250 in the casing cavity CC decreases and causes the refractive fluid 250 to contract, at least some of the refractive fluid flows from the deformable external fluid reservoir 290 to the casing cavity CC (e.g., so as to maintain the pressure of the refractive fluid 250 in the casing cavity CC at an approximately constant level).

In various implementations, rather than being included as part of the TAG lens 170B, the external reservoir configuration 280B may be configured as a separate element (e.g., as a separate accessory, or upgrade component for retrofitting an existing TAG lens, etc.). In such implementations, the external reservoir configuration 280B may be configured to be coupled to a tunable acoustic gradient (TAG) lens having a lens casing 210 with a casing cavity CC configured to contain an operational volume OPV of refractive fluid 250. The external reservoir configuration 280B may include a deformable external fluid reservoir 290B that is configured to contain refractive fluid 250 and a flow channel portion (e.g., including the channel portions 282B and 283B). The flow channel portion may be part of a flow channel FLC-B that connects the deformable external fluid reservoir 290B to the casing cavity CC of the TAG lens. The deformable external fluid reservoir 290B may contain a reserve volume RSV of the refractive fluid 250, and at least some of the refractive fluid 250 may be able to flow back and forth between the casing cavity CC and the deformable external fluid reservoir 290B through the flow channel FLC. The lens casing 210, the deformable external fluid reservoir 290B and the flow channel FLC-B may be configured as a sealed system.

In various implementations, a method is provided for preparing and operating the tunable acoustic gradient (TAG) lens 170B having the lens casing 210 with the casing cavity CC configured to contain the operational volume OPV of refractive fluid 250 and the controllable acoustic wave generating element 220 arranged inside the lens casing 210 around the optical path OPATH that passes through the operational volume OPV. In various implementations, the method includes adding refractive fluid 250 to the casing cavity CC and to the deformable external fluid reservoir 290B that is connected to the casing cavity CC by the flow channel FLC that passes through the lens casing 210. In various implementations, the lens casing 210 includes the inlet/outlet port 211 and the external reservoir configuration 280B includes the inlet/outlet port 284B which are each open while the refractive fluid 250 is added and through at least one of which the refractive fluid 250 is provided so as to be added to the casing cavity CC and to the deformable external fluid reservoir 290B. The inlet/outlet ports 211 and 284B are then each closed after the casing cavity CC is filled to contain the operational volume OPV of the refractive fluid 250, and the deformable external fluid reservoir 290B is filled to contain the desired reserve volume RSV of the refractive fluid 250 at a desired temperature of the refractive fluid 250 used for filling. In various implementations, it may be desirable that the deformable external fluid reservoir 290B is filled to contain a maximum desired reserve volume RSV of the refractive fluid 250 at a desired maximum operating or storage temperature of the TAG lens 170B. Once the inlet/outlet ports 211 and 284B are closed/sealed, the lens casing 210, the deformable external fluid reservoir 290B and the flow channel FLC-B are thus configured as a sealed system. In various implementations, during the filling and sealing process, all gas is excluded in the fluid-filled volume. The filled fluid may undergo an outgassing procedure in a vacuum chamber or the like, if desired, prior to sealing. Once the system is sealed, the TAG lens 170B may be controlled through normal operation to provide a periodically modulated optical power variation for the TAG lens 170B.

To be more explicit, in various implementations, the TAG lens 170 is configured with the sealed system nominally containing only the refractive fluid 250, and no intentional gas volume or intentional compressible component within the refractive fluid. More specifically, an intentional gas volume or intentional compressible component within the refractive fluid are defined as intentionally introduced elements comprising at least a minimum portion (e.g., 2%) of the total available fluid volume inside the lens casing 210, which intentionally displace or substitute for a comparable volume of refractive fluid 250 at the time that the casing cavity CC is filled with refractive fluid 250. In contrast, an incidental gas volume as defined herein comprises undesired gas that may arise due to outgassing or cavitation, or undesired leakage, and which does not qualify as an intentional gas volume (i.e., which in the present example would be a volume below 2% of the total available volume of the casing cavity CC).

In one specific example implementation, at an operating temperature of 20 degrees C., the TAG lens 170 is configured with the reserve volume RSV of refractive fluid 250 in the deformable external fluid reservoir 290 being less than 70% of a maximum design volume MDV of the deformable external fluid reservoir 290. As defined herein, a design volume is generally for a non-stressed and/or non-pressurized state. It will be appreciated that in such a configuration, when the temperature increases and the refractive fluid 250 expands, an amount of the refractive fluid 250 may flow from the casing cavity CC to the deformable external fluid reservoir 290, so as to increase the reserve volume RSV (e.g., while in certain implementations the operational volume OPV may remain approximately the same and approximately at the same pressure, such as approximately at 1 atmosphere). When the temperature decreases and the refractive fluid 250 contracts, an amount of the refractive fluid 250 may flow from the deformable external fluid reservoir 290 to the casing cavity CC, so as to decrease the reserve volume RSV (e.g., while in certain implementations the operational volume OPV may remain approximately the same and approximately at the same pressure, such as approximately at 1 atmosphere.)

In various implementations, a ratio of the maximum design volume MDV of the deformable external fluid reservoir 290 to the operational volume OPV of the refractive fluid 250 located inside the casing cavity CC may be at least 1/7. In various implementations, at an operating temperature of 20 degrees C., the TAG lens 170 may be configured with a ratio of the reserve volume RSV to the operational volume OPV of at least 1/10. It will be appreciated that such implementations provide margins for accommodating expansion and contraction of the refractive fluid 250, to enable the configuration to effectively operate over a range of operating temperatures. More specifically, in certain implementations, by enabling the refractive fluid 250 to flow back and forth between the casing cavity CC and the deformable external fluid reservoir 290, the reserve volume RSV may increase or decrease while keeping the operational volume OPV approximately the same and approximately at the same pressure (such as approximately at 1 atmosphere, etc.).

FIG. 5 is a diagram of a cross section of a TAG lens 170C with a second exemplary implementation of an external reservoir configuration 280C. As illustrated in FIG. 5, the external reservoir configuration 280C comprises an external reservoir body 281BC, an external reservoir top 281TC and a deformable external fluid reservoir 290C. In the example configuration of FIG. 5, the flow channel FLC-C comprises a tube TB-C that extends between the lens casing 210 and the deformable external fluid reservoir 290C, and through which the refractive fluid 250 may flow as previously outlined. In the example of FIG. 5, the tube TB-C includes a horizontal channel section TB-C1 and a vertical channel section TB-C2.

In the configuration of FIG. 5, the deformable external fluid reservoir 290C includes an upper neck portion 292C and a lower neck portion 293C. In various implementations, the upper and lower neck portions 292C and 293C may be relatively thick and solid except for a hole (e.g., in the middle) for accommodating the vertical channel section TB-C2 of the tube TB-C which extends through the upper and lower neck portions 292C and 293C. In various implementations, a clamp 289C may be clamped around the upper neck portion 292C, which secures the upper neck portion 292C around the vertical channel section TB-C2 of the tube TB-C. The lower neck portion 293C rests on or is secured by an indented portion 286C of the external reservoir body 281BC.

In various implementations, the vertical channel section TB-C2 of the tube TB-C may extend down past the end of the lower neck portion 293C into the deformable external fluid reservoir 290C, which may provide certain advantages (e.g., any incidental air bubbles that may arise in the deformable external fluid reservoir 290C will float up to the top below the lower neck portion 293C, and thus will be unlikely to flow into the vertical channel section TB-C2 of the tube TB-C). In addition, the horizontal channel section TB-C1 may extend into the lens casing 210 (e.g., into the reservoir exchange channel REC of the lens casing 210) and be secured (e.g., by adhesive or brazing) such that additional sealing elements (e.g., sealing rings) may not be required.

FIG. 6 is a diagram of a cross section of a TAG lens 170D with a third exemplary implementation of an external reservoir configuration 280D. In the example configuration of FIG. 6, the deformable external fluid reservoir 290D includes a piston 296D that moves in a first direction (e.g., downward) inside the external reservoir body 281BD when refractive fluid 250 expands and flows from the casing cavity CC to the deformable external fluid reservoir 290D, and that moves in a second direction (e.g., upward) that is opposite to the first direction when refractive fluid 250 contracts and flows from the deformable external fluid reservoir 290D to the casing cavity CC. One or more sealing elements 297D (e.g., sealing rings) may be included (e.g., as coupled to and/or located around the piston 296D) to ensure sealed containment of the refractive fluid 250 above the piston 296D. In various implementations, the deformable external fluid reservoir 290D further includes a spring 298D that is coupled to the piston 296D (e.g., to a lower portion of the piston 296D) to maintain an approximately constant mechanical spring rate for the piston 296D over a range of positions extending over at least 20 millimeters. It will be appreciated that such configurations with an approximately constant mechanical spring rate may be utilized to keep the reserve volume RSV in the deformable external fluid reservoir 290D and, correspondingly, the operational volume OPV in the casing cavity CC at an approximately constant pressure other than 1 atmosphere, if desired. It will be appreciated that a similar "unsealed" spring and piston arrangement could be implemented to press on a sealed bladder configuration (e.g., as previously outlined), to maintain the fluid in the sealed bladder (and the associated operational volume OPV in the casing cavity CC) at an approximately constant pressure other than 1 atmosphere, if desired.

FIG. 7 is a diagram of a top view of a TAG lens 170E with a fourth exemplary implementation of an external reservoir configuration 280E. In the configuration of FIG. 7, a deformable external fluid reservoir 290E (in a cylindrical donut shape) is contained within the external reservoir configuration 280E, and extends around at least a portion of the lens casing 210. As illustrated in the specific example configuration of FIG. 7, the deformable external fluid reservoir 290E extends around the entire circumference of the lens casing 210, although it will be appreciated that, in various alternative implementations, the deformable external fluid reservoir may extend around only a portion of the lens casing 210. It will be appreciated that such implementations may be formed with different overall external dimensions as compared to the implementations of FIGS. 4-7. The illustrated configuration may be more desirable or more convenient for mounting in certain applications.

The deformable external fluid reservoir 290E is connected to the casing cavity CC by one or more flow channels FLC-E through the lens casing 210. While only a single flow channel FLC-E is illustrated in FIG. 7, in alternative implementations multiple flow channels FLC may be disposed around the lens casing 210. The deformable external fluid reservoir 290E contains a reserve volume RSV-E of the refractive fluid 250. The flow channel FLC-E enables the refractive fluid 250 to flow back and forth between the casing cavity CC and the deformable external fluid reservoir 290E, in accordance with previously outlined principles. The lens casing 210, the deformable external fluid reservoir 290E and the flow channel FLC-E are configured as a sealed system. The lens casing 210 includes at least one inlet/outlet port 211, and the external reservoir configuration 280E includes at least one inlet/outlet port 284E, which may be utilized as described above for adding refractive fluid 250 to the TAG lens 170E. In various implementations, the external reservoir configuration 280E may be fixedly attached to the lens casing 210 utilizing various configurations (e.g., bolts, welding, etc.). The various volume relationships, filling methods, etc., may be implemented according to previously outlined principles, for the external reservoir configuration 280E.

FIG. 8 is a diagram of a top view of a TAG lens 170F with a fifth exemplary implementation of a dual external reservoir configuration 280F. In the example configuration of FIG. 8, external reservoir configurations 280F1 and 280F2 are disposed around the lens casing 210, including first and second deformable external fluid reservoirs 290F1 and 290F2, respectively.

The first and second deformable external fluid reservoirs 290F1 and 290F2 are connected to the casing cavity CC by first and second flow channels FLC-F1 and FLC-F2 through the lens casing 210, respectively. The first and second deformable external fluid reservoirs 290F1 and 290F2 contain first and second reserve volumes RSV-F1 and RSV-F2 of the refractive fluid 250, respectively, which together form a combined reserve volume RSV-F. The first and second flow channels FLC-F1 and FLC-F2 enable the refractive fluid 250 to flow back and forth between the casing cavity CC and the deformable external fluid reservoirs 290F1 and 290F2, respectively, according to previously outlined principles.

The lens casing 210, the first and second deformable external fluid reservoirs 290F1 and 290F2 and the first and second flow channels FLC-F1 and FLC-F2 are configured as a sealed system. The lens casing 210 includes at least one inlet/outlet port 211 and the external reservoir configurations 280F1 and 280F2 include respective inlet/outlet ports 284F1 and 284F2, which may be utilized as described above for adding refractive fluid 250 to the TAG lens 170F. In various implementations, the external reservoir configurations 280F1 and 280F2 may be fixedly attached to the lens casing 210 utilizing various configurations (e.g., bolts, welding, etc.). The various volume relationships (based on the combined volume (RSV-F1+RSV-F2), filling methods, etc., may be implemented according to previously outlined principles, for the external reservoir configuration 280F.

Figure 9:
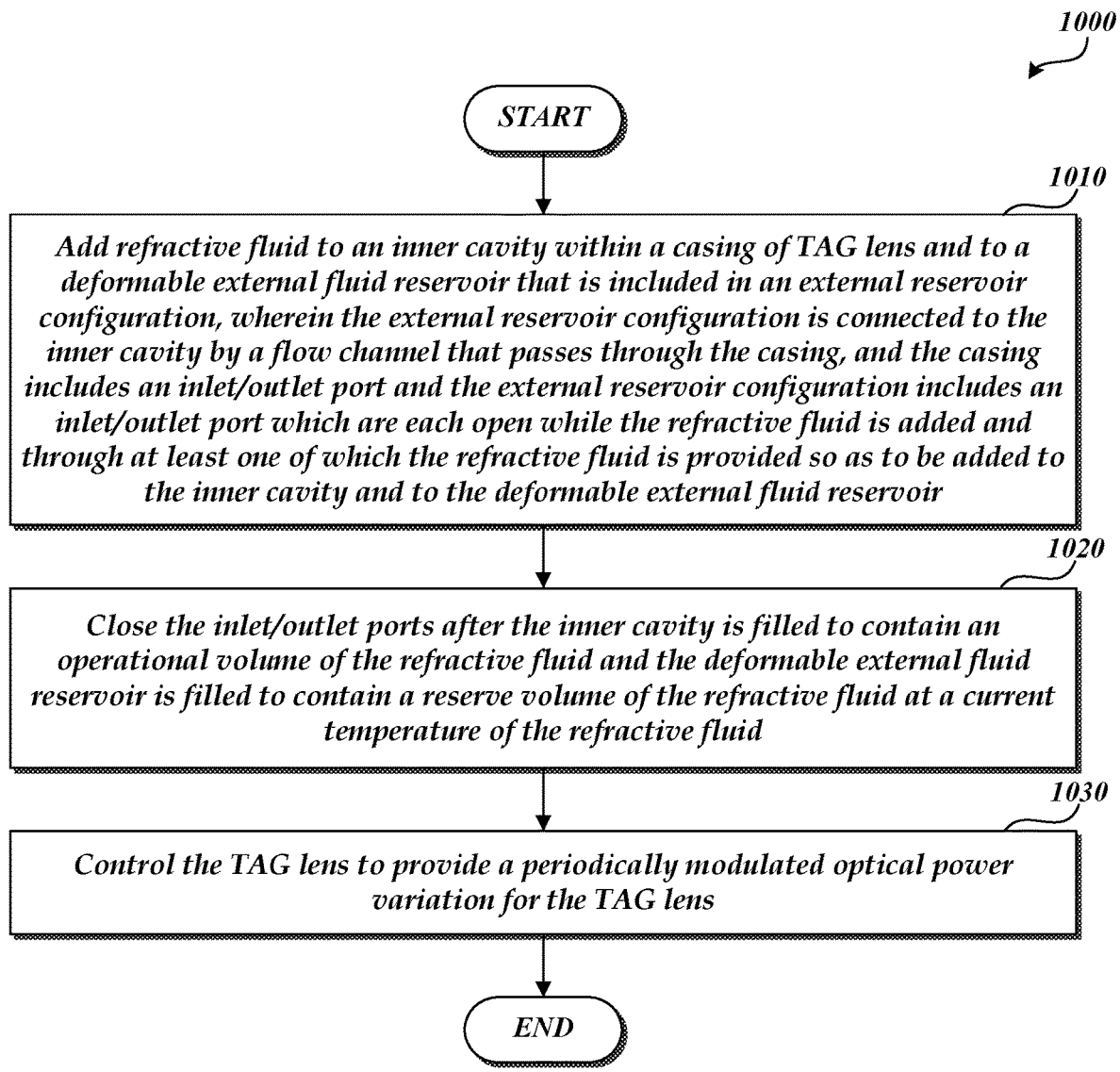
FIG. 9 is a flow diagram illustrating one exemplary implementation of a routine for preparing and operating a TAG lens with an external reservoir configuration according to principles disclosed herein.

FIG. 9 is a flow diagram illustrating one exemplary implementation of a routine 1000 for preparing and operating a TAG lens with an external reservoir configuration according to principles disclosed herein. As described above, in various implementations the TAG lens may have a lens casing with a casing cavity configured to contain an operational volume of refractive fluid, and a controllable acoustic wave generating element arranged inside the lens casing around an optical path that passes through the operational volume. As shown in FIG. 9, at a block 1010, refractive fluid is added to the casing cavity and to a deformable external fluid reservoir. The deformable fluid reservoir is included in the external reservoir configuration and is connected to the casing cavity by a flow channel that passes through the lens casing. The lens casing includes an inlet/outlet port, and the external reservoir configuration includes an inlet/outlet port, which are each open while the refractive fluid is added and through at least one of which the refractive fluid is provided so as to be added to the casing cavity and to the deformable external fluid reservoir.

Utilizing the implementation of FIG. 4 as an example configuration, the adding of the refractive fluid at block 1010 may initially include opening the vent 288B (e.g., which opens to the atmosphere) in addition to the inlet/outlet ports 211 and 284B. In one implementation, the refractive fluid is added through the inlet/outlet port 284B until the casing cavity CC is full and the deformable external fluid reservoir 290B is full, in that the reserve volume of refractive fluid in the deformable external fluid reservoir is at approximately 100% of the maximum design volume MDV, for which any air or other gasses may be expelled out of the inlet/outlet port 211 (e.g., for which there may essentially be a vacuum purge of the system that is to be sealed including an outgassing of any dissolved gas, etc.). (All of the foregoing may take place at a desired maximum operating or storage temperature of the TAG lens. Or alternatively, the system may be filled as outlined, at a lower temperature, and then fluid may be withdrawn out of the inlet/outlet port 284B in a manner that contracts the deformable external fluid reservoir 290B to a desired corresponding state.) In such an implementation, the inlet/outlet port 211 may then be sealed or closed. In various implementations, the amount of refractive fluid that is withdrawn may result in the reserve volume RSV-B of refractive fluid in the deformable external fluid reservoir 290B being less than 70% of the maximum design volume MDV of the deformable external fluid reservoir 290B at a desired operating temperature (e.g., such as 20 degrees C.), while the operational volume OPV in the casing cavity CC remains filled and approximately constant.

At a block 1020, the inlet/outlet ports are closed/sealed after the casing cavity is filled to contain the operational volume of the refractive fluid and the deformable external fluid reservoir is filled to contain the desired reserve volume of the refractive fluid at a current temperature of the refractive fluid. As described above with respect to the example of FIG. 4, in various implementations, the inlet/outlet ports may be closed at different times or in varying sequence, depending on the process for adding the refractive fluid. At a block 1030, after the system has been sealed, the TAG lens is controlled to provide a periodically modulated optical power variation for the TAG lens. For example, the controllable acoustic wave generating element may be controlled as described above to provide the periodically modulated optical power variation for the TAG lens.

While preferred implementations of the present disclosure have been illustrated and described, numerous variations in the illustrated and described arrangements of features and sequences of operations will be apparent to one skilled in the art based on this disclosure. Various alternative forms may be used to implement the principles disclosed herein. In addition, the various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

The invention claimed is:

1. A tunable acoustic gradient (TAG) lens comprising:
a lens casing having a casing cavity;
a refractive fluid, including an operational volume of the refractive fluid contained in the casing cavity;
a controllable acoustic wave generating element arranged inside the lens casing around an optical path that passes through the operational volume (e.g., a piezo);
an external reservoir configuration comprising a deformable external fluid reservoir that is connected to the casing cavity by a flow channel through the lens casing, wherein the deformable external fluid reservoir contains a reserve volume of the refractive fluid, and the flow channel enables the refractive fluid to flow back and forth between the operational volume and the reserve volume in accordance with expansion and contraction of the refractive fluid as occurs due to changes in an operating temperature of the TAG lens; and
wherein:
the operational volume of the refractive fluid is capable of changing its refractive index along the optical path in response to application of an acoustic wave by the acoustic wave generating element, and in accordance with which the TAG lens is controlled to provide a periodically modulated optical power variation for the TAG lens; and
the lens casing, the deformable external fluid reservoir and the flow channel are configured as a sealed system.

2. The TAG lens of claim 1, wherein the TAG lens is configured with the sealed system nominally containing only the refractive fluid and no intentional gas volume or intentional compressible component within the refractive fluid.

3. The TAG lens of claim 1, wherein, at an operating temperature of 20 degrees C., the TAG lens is configured with the reserve volume of the refractive fluid in the deformable external fluid reservoir being less than 70% of a maximum design volume of the deformable external fluid reservoir.

4. The TAG lens of claim 3, wherein a ratio of the maximum design volume of the deformable external fluid reservoir relative to the operational volume of the refractive fluid contained in the casing cavity is at least 1/7.

5. The TAG lens of claim 1, wherein, at an operating temperature of 20 degrees C., the TAG lens is configured with a ratio of the reserve volume relative to the operational volume of at least 1/10.

6. The TAG lens of claim 1, wherein the deformable external fluid reservoir comprises a deformable bladder that contains the reserve volume and that expands when the refractive fluid expands and flows from the casing cavity to the deformable external fluid reservoir and that contracts when the refractive fluid contracts and flows from the deformable external fluid reservoir to the casing cavity.

7. The TAG lens of claim 6, wherein the external reservoir configuration is configured with atmospheric pressure acting on an outside of the deformable bladder at all operating temperatures.

8. The TAG lens of claim 1, wherein the deformable external fluid reservoir is located to one side of an outside of the lens casing.

9. The TAG lens of claim 1, wherein the deformable external fluid reservoir extends around at least a portion of the lens casing.

10. The TAG lens of claim 1, wherein the deformable external fluid reservoir is a first deformable external fluid reservoir, the flow channel is a first flow channel and the reserve volume is a first reserve volume, and the external reservoir configuration further comprises a second deformable external fluid reservoir that is connected to the casing cavity by a second flow channel through the lens casing, wherein the second deformable external fluid reservoir contains a second reserve volume of the refractive fluid, and the flow channel enables the refractive fluid to flow back and forth between the operational volume and the second reserve volume in accordance with expansion and contraction of the refractive fluid as occurs due to changes in the operating temperature of the TAG lens, and wherein the lens casing, the first and second deformable external fluid reservoirs and the first and second flow channels are configured as a sealed system.

11. The TAG lens of claim 1, wherein the deformable external fluid reservoir comprises a piston that moves in a first direction when the refractive fluid expands and flows from the casing cavity to the deformable external fluid reservoir and that moves in a second direction that is opposite to the first direction when the refractive fluid contracts and flows from the deformable external fluid reservoir to the casing cavity.

12. The TAG lens of claim 11, wherein the deformable external fluid reservoir further comprises a spring that is coupled to the piston to maintain an approximately constant mechanical spring rate for the piston over a range of positions extending over at least 20 millimeters.

13. The TAG lens of claim 1, wherein the lens casing comprises a reservoir exchange channel that is included as part of the flow channel.

14. The TAG lens of claim 1, wherein the flow channel comprises a tube that extends between the lens casing and the deformable external fluid reservoir and through which the refractive fluid is enabled to flow back and forth between the operational volume and the reserve volume.

15. The TAG lens of claim 1, wherein the flow channel includes a flow restricting section that has a cross-sectional flow area of at most 25 square millimeters.

16. The TAG lens of claim 15, wherein the flow restricting section has a cross-sectional flow area of at most 15 square millimeters.

17. The TAG lens of claim 1, wherein the deformable external fluid reservoir is configured to maintain an approximately constant pressure of the refractive fluid in the casing cavity over at least a range of temperatures between −20 degrees C. and 60 degrees C.

18. The TAG lens of claim 1, wherein the external reservoir configuration further comprises a vent for venting to an external atmosphere and which maintains the refractive fluid in the casing cavity at a pressure of approximately 1 atmosphere regardless of the operating temperature of the TAG lens.

19. The TAG lens of claim 1, wherein the lens casing comprises at least one inlet/outlet port and the external reservoir configuration comprises at least one inlet/outlet port that are utilized in combination for initially adding the refractive fluid to at least one of the lens casing or the deformable external fluid reservoir, wherein the inlet/outlet ports are sealed after the refractive fluid is filled to an initial level.

20. The TAG lens of claim 1, wherein a ratio of the operational volume to the reserve volume varies depending at least in part on a temperature of the refractive fluid.

21. The TAG lens of claim 20, wherein the deformable external fluid reservoir is configured to maintain an approximately constant pressure of the refractive fluid in the casing cavity such that when the temperature of the refractive fluid increases and causes the refractive fluid to expand, at least some of the refractive fluid flows from the casing cavity to the deformable external fluid reservoir.

22. The TAG lens of claim 20, wherein the deformable external fluid reservoir is configured to maintain an approximately constant pressure of the refractive fluid in the operational volume such that when the temperature of the refractive fluid decreases and causes the refractive fluid to contract, at least some of the refractive fluid flows from the deformable external fluid reservoir to the casing cavity.

23. The TAG lens of claim 1, wherein the TAG lens is included as part of a vision system and the control of the TAG lens to provide a periodically modulated optical power variation for the TAG lens correspondingly provides a focus distance variation for the vision system.

24. An external reservoir configuration configured to be coupled to a tunable acoustic gradient (TAG) lens having a lens casing with a casing cavity configured to contain an operational volume of refractive fluid and a controllable acoustic wave generating element arranged inside the lens casing around an optical path that passes through the operational volume, wherein the operational volume of the refractive fluid is capable of changing its refractive index along the optical path in response to application of an acoustic wave by the acoustic wave generating element, and in accordance with which the TAG lens is controlled to provide a periodically modulated optical power variation for the TAG lens, the external reservoir configuration comprising:
  a deformable external fluid reservoir that is configured to contain refractive fluid; and
  a flow channel portion that is part of a flow channel that connects the deformable external fluid reservoir to the casing cavity of the TAG lens, wherein the deformable external fluid reservoir contains a reserve volume of the refractive fluid, and at least some of the refractive fluid is able to flow back and forth between the casing cavity and the deformable external fluid reservoir through the flow channel; and
  wherein the lens casing, the deformable external fluid reservoir and the flow channel are configured as a sealed system.

25. A method for preparing and operating a tunable acoustic gradient (TAG) lens having a lens casing with a casing cavity configured to contain an operational volume of refractive fluid and a controllable acoustic wave generating element arranged inside the lens casing around an optical path that passes through the operational volume, the method comprising:
- adding the refractive fluid to the casing cavity and to a deformable external fluid reservoir that is included in an external reservoir configuration and is connected to the casing cavity by a flow channel that passes through the lens casing, wherein the lens casing includes an inlet/outlet port and the external reservoir configuration includes an inlet/outlet port which are each open while the refractive fluid is added and through at least one of which the refractive fluid is provided so as to be added to the casing cavity and to the deformable external fluid reservoir;
- closing the inlet/outlet ports after the casing cavity is filled to contain the operational volume of the refractive fluid and the deformable external fluid reservoir is filled to contain a reserve volume of the refractive fluid at a current temperature of the refractive fluid; and
- controlling the TAG lens to provide a periodically modulated optical power variation for the TAG lens.

26. The method of claim 25, wherein:

the adding of the refractive fluid to the casing cavity and to the deformable external fluid reservoir comprises:
- filling the casing cavity until it is full and filling the deformable external fluid reservoir until it is full in that the reserve volume of the refractive fluid in the deformable external fluid reservoir is at approximately 100% of a maximum design volume MDV, after which the inlet/outlet port of the lens casing is closed; and
- withdrawing out of the inlet/outlet port of the external reservoir configuration an amount of refractive fluid such that the reserve volume of the refractive fluid in the deformable external fluid reservoir is less than 70% of the maximum design volume of the deformable external fluid reservoir at 20 degree C.; and the closing the inlet/outlet ports comprises:
- closing the inlet/outlet port of the lens casing after the casing cavity is filled to contain the operational volume of the refractive fluid; and
- closing the inlet/outlet port of the deformable external fluid reservoir after the amount of refractive fluid is withdrawn such that the reserve volume of the refractive fluid in the deformable external fluid reservoir is less than 70% of the maximum design volume of the deformable external fluid reservoir at 20 degrees C.

* * * * *